United States Patent [19]

Roberts et al.

[11] Patent Number: 5,061,628
[45] Date of Patent: Oct. 29, 1991

[54] RESTRICTION ENDONUCLEASE FSEI

[75] Inventors: Richard J. Roberts, Cold Spring Harbor; Janise L. Meyertons, Centerport, both of N.Y.; Mary P. Lechevalier, Piscataway, N.J.

[73] Assignees: Rutgers University, Piscataway, N.J.; Cold Spring Harbor Laboratory, Cold Spring Harbor, N.Y.

[21] Appl. No.: 381,460

[22] Filed: Jul. 18, 1989

[51] Int. Cl.$^5$ .......................... C12N 9/22; C12P 19/34
[52] U.S. Cl. ........................................ 435/199; 435/91
[58] Field of Search .................................. 435/199, 91

[56] References Cited

PUBLICATIONS

Roberts, R. J. (1989) Nuc. Acids Res. 17 (suppl), r347, r356, r373.
Wilson, G. C. (1988), Gene 74, 281–289.
Roberts, Richard J., "Restriction Enzymes and Their Isochizomers", *Nucleic Acids Research*, (1988) 16:271–313.

Primary Examiner—Elizabeth C. Weimar
Assistant Examiner—Charles L. Patterson
Attorney, Agent, or Firm—Barbara Rae-Venter

[57] ABSTRACT

A novel Type II restriction endonuclease isolated from Frankia species DDB13250120 is provided. The enzyme, designated FseI, recognizes the octanucleotide sequence

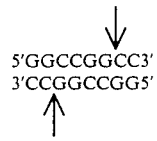

and cleaves Adenovirus 2 DNA at the sites indicated by the arrows.

13 Claims, No Drawings

RESTRICTION ENDONUCLEASE FSEI

INTRODUCTION

1. Technical Field

This invention relates to a new Type II restriction endonuclease designated FseI.

2. Background

The ability to specifically cleave a duplex DNA molecule into discrete fragments is essential for the manipulation of DNA in vitro. Such specific cleavage is accomplished using restriction endonucleases which are enzymes capable of cutting a DNA molecule at or about a specific recognition site. Type II restriction endonucleases recognize and cleave DNA at site-specific sequences which often have an axis of rotational symmetry. The site of cleavage may be within the recognition sequence or may lie a fixed number of base pairs away from the sequence. Moreover, the cleavage may be cut straight across the duplex producing flush or blunt-ended fragments, or may be staggered to produce either 5'- or 3'- cohesive ends.

To perform genetic manipulation in vitro and for mapping of a cell genome it is desirable to have a very large number of restriction endonucleases to cleave at preselected locations. Most restriction enzymes have recognition sites containing 4-6 bases. However, the use of restriction enzymes whose recognition sites contain a larger number of bases are of interest, since fewer and larger fragments of DNA are likely to be generated by treatment with such restriction enzymes. More contiguous genes can thus be visualized on a single fragment and the fragments generated are fewer and therefore more easily separated from each other.

Relevant Literature

Many restriction enzymes are reported in the literature. Two other restriction enzymes have been described which recognize 8 bases, SfiI, Qiang, et al., *Nucleic Acids Res.* (1984) 12:4507 and NotI, Barsetti, et al., (unpublished) quoted in Roberts *Nucleic Acids Res.* (1984) 12:r167-r204. For a compilation of restriction enzymes and their isoschizomers, see, for example, Roberts *Nucleic Acids Research* (1988) 16:271-313 (supplement).

SUMMARY OF THE INVENTION

A novel restriction enzyme obtained from the bacterial strain Frankia sp. DDB13250120 is provided. The endonuclease designated FseI, recognizes the sequence

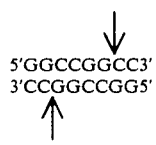

where the arrow indicates the cleavage site in Adenovirus 2 DNA. FseI digests Adenovirus 2 DNA into four fragments. The DNA of SV40, 0X174, bacteriophages lambda and T7, and plasmids pBR322 and pUC18 are not cleaved by FseI. FseI can be isolated at a high degree of purity, being substantially free from contaminating exonuclease and endonuclease activities.

DESCRIPTION OF SPECIFIC EMBODIMENTS

Restriction endonuclease FseI is a Type II restriction enzyme which can be isolated from bacterial strain Frankia sp. DDB13250120. The enzyme has been named in accordance with the nomenclature for Frankia of Lechevalier *Canadian J. of Botany* (1983) 61:2964-2967. FseI can be characterized as recognizing and cleaving the octanucleotide sequence GGCCGGCC; optimal enzyme activity is obtained at about 26°-28° C. in NaCl restriction buffer or KGB buffer. The enzyme is further characterized as capable of cleaving Adenovirus 2 DNA into four fragments, the cleavage site within the recognition sequence being as indicated by the arrows

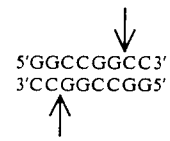

FseI may be obtained in a variety of ways. It is available from naturally occurring sources, such as Frankia sp. DDB13250120. Isolation of the enzyme may be performed using, for example, the purification procedure of Myertons, et al., *J. Industrial Microbiology* (1987) 2:293-303. Cells are grown in a suitable culture medium, e.g., Bennett's broth, pelleted, for example by centrifugation, and suspended in an extraction buffer. The cell walls are lysed by brief incubation of the cells with lysozyme followed by disruption in a French pressure cell or sonication. The cell lysate is cleared of cell debris and unbroken cells by centrifugation, and the supernatant decanted. DNA and RNA are removed, for example, by precipitation with streptomycin sulfate. The enzyme may be isolated from the supernatant by ion-exchange chromatography followed by Fast Protein Liquid Chromatography (FPLC). Active fractions, as measured by ability to cleave Adenovirus 2 DNA, are pooled and dialyzed, and the concentrated enzyme may be stored at −20° C. or −70° C. The enzyme preparation obtained by this procedure is substantially free from contaminating exonuclease and endonuclease activity.

Other techniques of enzyme purification may also find use; these techniques can include solvent extraction, gel permeation chromotography, reversed phase-HPLC, electrophoresis, or the like. For active fragments, various synthetic techniques may be employed, where the polypeptide will be synthesized on a solid support. A number of commercial synthesizers are available and may be used to advantage, for example, from SmithKline-Beckman, Applied Biosystems, etc.

FseI may also be purified, whether from natural or synthetic sources, using affinity chromatography, either by the use of, for example, immobilized Adenovirus 2 DNA, or fragments thereof capable of binding to FseI, or by the use of antibodies to FseI, or fragments thereof which can be coupled to a solid support in conventional ways, For antibodies. either polyclonal or monoclonal antibodies may be used. The antibodies can be prepared in conventional ways, either by using FseI or fragments thereof as an immunogen and injecting it into a mammalian host, e.g. mouse, cow, goat, sheep, rabbit, etc., particularly with an adjuvant, e.g. complete Freunds adjuvant, aluminum hydroxide gel, or the like. The host may then be bled and the blood employed for isolation of polyclonal antibodies, or in the case of the mouse, the peripheral blood lymphocytes or splenic lymphocytes (B-cells) employed for fusion with an appropriate myeloma cell to immortalize the chromosomes for monoclonal expression of antibodies specific for FseI. The antibodies can also be used to screen other cells for the presence of FseI, or enzymes having at least substantial homology usually differing by fewer than 5% of the amino acids, which may also recognize the octanucleotide sequence 5'GCCCGGCC3'.

In use, substrate DNA may be restricted by FseI in a suitable buffer, e.g., Tris-HCl pH=7.6, 10 mM MgCl$_2$, 50 mM NaCl, 10 mM $\beta$- mercaptoethanol, 100 $\mu$g/ml bovine serum albumin or KGB buffer: 200 mM potassium glutamate, 50 mM tris-acetate pH=7.6, 20 mM magnesium acetate, 1 mM $\beta$-mercaptoethanol and 100 $\mu$g/ml bovine serum albumin, at 37° C. for a suitable time, e.g., 1 hour. McClelland, et al., *Nucleic Acids Res.* (1988) 16:364.

The recognition sequence for the restriction endonuclease can be determined by digesting susceptible DNA with the restriction enzyme alone and in conjunction with other restriction enzymes. The cut sites on the DNA in these double digests can be used to determine the recognition sequence; the primed synthesis reaction can be used to characterize the cleavage site. In this way it can be determined that the recognition sequence is an octanucleotide which comprises the bases guanine and cytosine. When using Adenovirus 2 DNA as substrate DNA, the probable sequence of the octanucleotide is 5'-GCCCGGCC-3' and the cleavage site is as indicated by the arrows

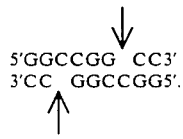

Fsel finds application in the genetic engineering of prokaryotes and eukaryotes for production of medical and industrial products. FseI also finds use in determining restriction fragment polymorphisms in human diseases and in mapping of cellular genomes.

The following examples are offered by way of illustration and not by way of limitation.

EXPERIMENTAL

Frankia sp. DDB132501250 was deposited in the *Agricultural Research Service Culture, Collection* (NRRL), 1815 N. University Street, Peoria, Ill. on July 28, 1989 and given Accession number NRRL 18528.

EXAMPLE

Isolation and Characterization of FseI Growth of Cells and Preparation of Cell Extract Frankia cells were incubated statically at 27°-30° C. for three to four weeks in a nutrient medium. The cells were harvested by centrifugation and resuspended in a solution containing 10 mM Tris-HCl pH-8.0, 1 mM EDTA and 50% glycerol. Cells were frozen at −70° C. until processing for the enzyme. The frozen pellet was thawed, and the cells are fractured in a French pressure cell (1×at 1300 psi). The crude extract was centrifuged to remove cell debris. A solution of 20% Streptomycin sulfate in 100 mM Tris-HCl, pH 8.0 was then added to the supernatant to a final concentration of 2% to precipitate RNA and DNA. The supernatant was clarified by centrifugation and then purified as follows.

DEAE-52 Chromatography

The crude extract was loaded onto a 1.0 cm×10 cm DEAE-52 column equilibrated with Buffer A (10 mM potassium phosphate, pH 7.4, 10 mM ($\beta$-mercaptoethanol, 0.1 M EDTA, 10% (v/v) glycerol). The restriction enzyme was eluted from the column with a linear 0–1.0M KCl-buffer A gradient. One ml fractions were collected and assayed for activity by observing digestion of Adenovirus 2 DNA. FseI activity eluted between fractions 13 and 16.

FPLC

The active fractions from the DEAE-52 column were pooled and dialyzed against Buffer B (20 mM tris-HCl pH=7.5, 1 mM EDTA pH=8.0, 10% (v/v) glycerol, 10 mM $\beta$-mercaptoethanol). The restriction enzyme was further fractionated using FPLC, using the Mono Q anion-exchange column (Pharmacia). Partially purified enzyme was eluted from the FPLC column using a 0–1 M KCl-buffer B linear gradient. One ml fractions were collected and assayed for activity by observing digestion of Adenovirus 2 DNA. The active fractions (elution occurs within 1 hour) were pooled, adjusted to a final concentration of 50% glycerol and stored at −20° C.

FseI Assay Conditions

To assay for FseI activity, suitable dilutions of the FPLC-column purified enzyme were incubated with Adenovirus 2 DNA in either Nacl or KGB restriction buffers at 26°-28° C. for from one hour to overnight. The reactions were terminated by the addition of Ficoll stop dye (0.25% bromophenol blue, 15% Ficoll type 400 and 50 mM EDTA) and by heating the reaction to 65° C. for 5 minutes. The DNA fragments were separated by electrophoresis at 80 volts for several hours in a 0.8% agarose gel containing 1 $\mu$g/ml ethidium bromide.

Characterization of FseI

Complete FseI digests of Adenovirus 2 DNA allowed sizes to be assigned to the four fragments obtained. Comparison of the approximate fragment sizes with the Adenovirus 2 genome nucleotide sequence allowed GGCCGGCC to be assigned as the probable recognition sequence for FseI. Mapping of the cleavage sites to specific regions of the Adenovirus 2 genome was achieved by performing FseI digests on Adenovirus 2 DNA alone and in conjunction with other restriction enzymes. These double digests localized the cut sites on the DNA and confirmed the recognition site as GGCCGGCC.

The primed-synthesis reaction was used to characterize the FseI cleavage site. An M13 clone containing a segment of the Adenovirus 2 genome with an FseI site was extended using dideoxynucleoside triphosphates for the chain termination sequencing reaction. The primed-synthesis reaction was cleaved with FseI, and the resulting single band, when compared to the control lanes of G, A, T, C, indicated that DNA cleavage of Adenovirus 2 DNA occurred in the site

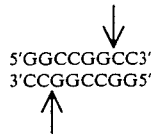

as indicated by the arrows. To determine the type of cut created, the primed-synthesis reaction cleaved with FseI was incubated with DNA polymeraseI-Klenow fragment. A comparison of the single fragment obtained and the control lanes of G, A, T, C, indicated that FseI cleaves to produce cohesive DNA ends with a four-base 3' extension.

The pH and temperature optimum, and the ideal assay conditions were tested. The pH range examined was pH=6.0–8.5. The temperature range investigated was 25°–37° C. Ten different assay buffers were checked. The pH for optimum enzyme activity was pH=7.6 and the ideal temperature was in the range 26°–28° C. The optimum restriction buffers were Nacl and KGB as described above.

According to the subject invention, a novel restriction endonuclease is provided which is capable of cleaving the sequence 5'GGCCGGCC-3'. The enzyme may be isolated from Frankia species DDB13250120 substantially free from contaminating enzymes. Most restriction enzymes recognize sequences of four to six nucleotides, hence when they cleave large genomes many small, indiscernible fragments of DNA are produced. Cleavage of large genomes by FseI will yield fewer and larger DNA fragments which can be better resolved by gel electrophoresis. In addition, several contiguous genes can be isolated on a single fragment. The use of FseI is thus advantageous for mapping large genomes, such as the *E. coli* genome and the human genome.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A restriction endonuclease capable of recognizing and cleaving DNA comprising an octanucleotide having the sequence 5'-GGCCGGCC-3'.

2. The restriction endonuclease according to claim 1, wherein said DNA is Adenovirus 2 DNA and said octanucleotide is cleaved at a position indicated by the arrows:

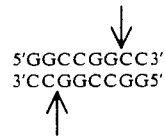

3. The restriction endonuclease according to claim 2, obtained by isolation from a culture of Frankia sp. DDB13250120.

4. A restriction endonuclease characterized as having a recognition sequence which comprises the octanucleotide 5'GGCCGGCC-3' and which is capable of being isolated from a culture of Frankia sp. DDB13250120.

5. The restriction endonuclease according to claim 4, wherein said endonuclease cleaves DNA comprising said recognition sequence at a position indicated by the arrows:

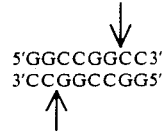

6. The restriction endonuclease according to claim 5, wherein said DNA is Adenovirus 2 DNA.

7. A restriction endonuclease having at least substantially the same amino acid sequence as FseI obtainable from Frankia sp. DDB13250120.

8. The restriction endonuclease according to claim 7, wherein said endonuclease recognizes and cleaves a DNA sequence comprising 5'GGCCGGCC3'.

9. A restriction endonuclease according to claim 4, wherein said endonuclease is obtained by isolation from a culture of Frankia DDB13250120.

10. A method for obtaining a restriction endonuclease which recognizes and cleaves the octanucleotide 5'-GGCCGGCC-3', said method comprising:
  lysing cells of Frankia sp. DDB13250120;
  freeing the resulting lysate of cell debris; and
  isolating said endonuclease from the supernatant.

11. The restriction endonuclease according to claim 10, wherein said restriction enzyme is FseI.

12. FseI prepared in accordance with the method of claim 10.

13. A restriction endonuclease prepared by the method of claim 10 and which is at least substantially free from contaminating exonuclease and endonuclease activity.

* * * * *

UNITED STATES PATENT AND TRADEMARK OFFICE
CERTIFICATE OF CORRECTION

PATENT NO. : 5,061,628

DATED : October 29, 1991

INVENTOR(S) : Roberts et al

It is certified that error appears in the above-identified patent and that said Letters Patent is hereby corrected as shown below:

ON THE TITLE PAGE

At [57], after, "arrows." insert the following new paragraph

--This invention was made with governmnet support under Grant No. R01 HG00303 awarded by the National Institutes of Health. The Government has certain rights in the invention.

Signed and Sealed this

Twentieth Day of July, 1993

Attest:

MICHAEL K. KIRK

*Attesting Officer*          *Acting Commissioner of Patents and Trademarks*